(12) United States Patent
Fudge et al.

(10) Patent No.: US 9,931,054 B2
(45) Date of Patent: Apr. 3, 2018

(54) LOW DEAD SPACE LIQUID TRAP

(71) Applicant: KONINKLIJKE PHILIPS N.V., Eindhoven (NL)

(72) Inventors: Brian Matthew Fudge, Middlefield, CT (US); David Scampoli, South Glastonbury, CT (US)

(73) Assignee: Koninklijke Philips N.V., Eindhoven (NL)

( * ) Notice: Subject to any disclaimer, the term of this patent is extended or adjusted under 35 U.S.C. 154(b) by 316 days.

(21) Appl. No.: 14/428,381

(22) PCT Filed: Sep. 16, 2013

(86) PCT No.: PCT/IB2013/058576
§ 371 (c)(1),
(2) Date: Mar. 16, 2015

(87) PCT Pub. No.: WO2014/045182
PCT Pub. Date: Mar. 27, 2014

(65) Prior Publication Data
US 2015/0223728 A1    Aug. 13, 2015

Related U.S. Application Data

(60) Provisional application No. 61/703,416, filed on Sep. 20, 2012.

(51) Int. Cl.
*A61B 5/08* (2006.01)
*A61B 5/097* (2006.01)
(Continued)

(52) U.S. Cl.
CPC ............... *A61B 5/082* (2013.01); *A61B 5/097* (2013.01); *A61M 16/0051* (2013.01); *A61M 16/085* (2014.02); *A61M 16/0808* (2013.01); *A61M 16/0833* (2014.02); *B01D 53/14* (2013.01); *B01D 53/229* (2013.01);
(Continued)

(58) Field of Classification Search
CPC ................................ A61B 5/082; A61B 5/097
See application file for complete search history.

(56) References Cited

U.S. PATENT DOCUMENTS 5,131,387 A * 7/1992 French ................... A61B 5/097
128/205.12
5,357,972 A * 10/1994 Norlien ................... A61B 5/097
600/538
(Continued)

FOREIGN PATENT DOCUMENTS

| CN | 2326188 Y | 6/1999 |
| CN | 1180997 A | 4/2004 |

(Continued)

*Primary Examiner* — Puya Agahi

(57) ABSTRACT

A low dead space liquid trap includes: a tube, having an inlet, an outlet, and an aperture disposed between the inlet and the outlet at a bottom of the tube, wherein the tube defines a channel extending in a first direction between the inlet and the outlet, the channel having a cross section perpendicular to the first direction; a reservoir disposed beneath the aperture of the tube; and a gas permeable membrane extending across the channel at an angle greater than zero with respect to the cross section of the channel.

17 Claims, 5 Drawing Sheets

(51) Int. Cl.
*A61M 16/00* (2006.01)
*A61M 16/08* (2006.01)
*B01D 53/14* (2006.01)
*B01D 53/22* (2006.01)
*A61M 16/10* (2006.01)

(52) U.S. Cl.
CPC ..... *A61M 16/105* (2013.01); *A61M 2016/103* (2013.01); *A61M 2230/432* (2013.01); *A61M 2230/50* (2013.01); *B01D 2053/221* (2013.01)

(56) References Cited

U.S. PATENT DOCUMENTS

| | | | |
|---|---|---|---|
| 6,585,661 B1 * | 7/2003 | Hunt | A61B 5/087 600/532 |
| 8,414,682 B2 | 4/2013 | Larsen et al. | |
| 9,417,222 B2 | 8/2016 | Matsubara et al. | |
| 2006/0090645 A1 | 5/2006 | Kent | |
| 2007/0193584 A1 * | 8/2007 | Laurila | A61M 16/08 128/205.12 |
| 2008/0091116 A1 | 4/2008 | Cardell et al. | |
| 2008/0196715 A1 * | 8/2008 | Yamamori | A61B 5/0836 128/203.12 |
| 2009/0137920 A1 | 5/2009 | Colman et al. | |
| 2009/0312662 A1 * | 12/2009 | Colman | A61B 5/097 600/543 |
| 2010/0089399 A1 | 4/2010 | Landis et al. | |
| 2010/0154797 A1 * | 6/2010 | Landis | A61M 16/0463 128/205.27 |
| 2011/0283884 A1 * | 11/2011 | Larsen | A61M 16/1065 95/25 |

FOREIGN PATENT DOCUMENTS

| | | |
|---|---|---|
| EP | 1820529 A1 | 8/2007 |
| JP | H07120462 A | 5/1995 |

* cited by examiner

LOW DEAD SPACE LIQUID TRAP

CROSS-REFERENCE TO RELATED APPLICATIONS

This application is a national stage application under 35 U.S.C. § 371 of International Application No. PCT/IB2013/058576 filed on Sep. 16, 2013 and published in the English language on Mar. 27, 2014 as International Publication No. WO 2014/045182 A1, which claims priority to U.S. Application No. 61/703,416 filed on Sep. 20, 2012, the entire disclosures of which are incorporated herein by reference.

TECHNICAL FIELD

This invention pertains to a low dead space liquid trap, for example a liquid trap that may be employed in a sidestream monitoring arrangement which measures one or more characteristics of a patient's respiratory gas.

BACKGROUND AND SUMMARY

It is often desirable to measure one or more characteristics of a patient's respiratory gas, for example a patient under ventilation or anesthesia, or connected to an external air or oxygen supply. In particular, it is often desirable to measure carbon dioxide ($CO_2$) levels in the respiratory gas of a patient.

Capnography monitors the concentration or partial pressure of $CO_2$ in the respiratory gas of a patient and provides a graphic display of instantaneous $CO_2$ concentration ($FCO_2$) versus time or expired volume during a respiratory cycle. This display may be referred to as a $CO_2$ waveform or capnogram. Similarly, capnometry measures and displays carbon dioxide ($CO_2$) levels on a digital or analog monitor, for example showing the maximum inspiratory and expiratory $CO_2$ concentrations during a respiratory cycle. Capnography (or capnometry) may be employed in a hospital setting, for example, to display $CO_2$ levels in the respiratory gas of a ventilated patient, such as during procedural sedation. Capnography has been employed as a standard of monitoring during anesthesia for more than three decades.

Capnography is also increasingly being used by paramedics to aid in their assessment and treatment of patients in the prehospital environment. These uses include verifying and monitoring the position of an endotracheal tube. A properly positioned tube in the trachea guards the patient's airway and enables the paramedic to provide ventilation for the patient. A misplaced tube in the esophagus can lead to death. A study in the March 2005 Annals of Emergency Medicine, comparing field intubations that used continuous capnography to confirm intubations versus non-use showed zero unrecognized misplaced intubations in the monitoring group versus 23% misplaced tubes in the unmonitored group. The American Heart Association (AHA) affirmed the importance of using capnography to verify tube placement in their 2010 ACLS/CPR Guidelines.

The AHA also notes in their new guidelines that capnography, which indirectly measures cardiac output, can also be used to monitor the effectiveness of CPR and as an early indication of return of spontaneous circulation (ROSC). Studies have shown that when a person doing CPR tires, the patient's end-tidal $CO_2$ ($ETCO_2$), the level of carbon dioxide released at the end of expiration) falls, and then rises when a fresh rescuer takes over. Other studies have shown when a patient experiences return of spontaneous circulation, the first indication is often a sudden rise in the $ETCO_2$ as the rush of circulation washes untransported $CO_2$ from the tissues. Likewise, a sudden drop in $ETCO_2$ may indicate the patient has lost their pulse and CPR may need to be initiated.

Capnography, because it provides a breath by breath measurement of a patient's ventilation, can quickly reveal a worsening trend in a patient's condition by providing paramedics with an early warning system into a patient's respiratory status. Paramedics are also now also monitoring the $ETCO_2$ status of nonintubated patients by using a nasal cannula that collects the carbon dioxide. A high $ETCO_2$ reading in a patient with altered mental status or severe difficulty breathing may indicate hypoventilation and a possible need for the patient to be intubated. Similarly, a low $ETCO2$ reading in some patients, may indicate hyperventilation.

In general, there are two types of arrangements which are employed for capnography: mainstream (non-diverting) capnography monitoring and sidestream (diverting) capnography monitoring. Sidestream, or diverting, capnography transports a portion of a patient's respiratory gas from the sampling site, through a sampling tube, to the sensor, whereas mainstream, or non-diverting, capnography does not transport gas away from the sampling site. In other words, one can view the difference between mainstream (non-diverting) capnography and sidestream (diverting) capnography as clinically measuring $CO_2$ at the sample site versus measuring $CO_2$ in the monitor distant from the sample site.

With mainstream monitoring, the sensor is located on a special airway adapter so that $CO_2$ is measured directly in the patient's breathing circuit. Advantages of mainstream monitoring include faster response time, the ability to measure gas near Body Temperature and Pressure Saturated (BTPS) conditions, and operation without a water trap. However, in general mainstream monitoring has some drawbacks. Such drawbacks include the inability to monitor non-intubated patients easily.

In sidestream capnography, a sample of the patient's respiratory gas is aspirated from the breathing circuit to a sensor residing inside the monitor. In general, sidestream monitoring has some drawbacks in comparison to mainstream monitoring, including for example sample line occlusion and waveform distortions. Furthermore, the temperature of the sampled gas decreases toward room temperature during its transit from the patient connection to the monitor. This results in condensate forming on the walls of the tubing and a resulting decrease in the partial pressure of water vapor from the BTPS value to much lower values. This decrease in water vapor pressure can cause an apparent increase in $CO_2$ concentration.

However, sidestream configurations may be used with both intubated and non-intubated patients. Accordingly, sidestream monitoring is often employed instead of mainstream monitoring, particularly in the case of non-intubated patients, .

One of the primary challenges in sidestream monitoring is separating any condensed liquid (e.g., water) from the gas sample and preventing the liquid from entering the gas monitoring device where it can damage the sensor. Most water traps available on the market today are for sampling systems with flow rates in the range of 100 ml/min or more. However with some patient groups, it is often desirable to operate with lower flow rates, for example on the order of 40-60 ml/minute.

Moreover, many water traps also require the use of a secondary flow to pull a negative pressure in the reservoir of the water trap to help separate the liquid from the gas sample.

Unfortunately, the commonly available water traps have too much dead space and volume, and the resulting impact on the gas sample characteristics is detrimental to the system performance. In particular, the gas measurement accuracy, respiratory rate range, and signal fidelity are all negatively impacted by a large dead space in a water trap in a sidestream capnography system.

Furthermore, the need for a large breath sample rate has inhibited use of sidestream monitoring in low-flow applications.

Accordingly, it would be desirable to provide a water trap which can address one or more of the issues described above.

In one aspect of the invention, a device comprises: a separation chamber and a reservoir. The separation chamber has an inlet configured to receive a gas sample from a patient; an outlet configured to output the gas sample; and an aperture disposed between the inlet and the outlet at a bottom of the separation chamber. The separation chamber defines a channel extending in a first direction between the inlet and the outlet and is configured to pass the gas sample through the channel from the inlet to the outlet. The reservoir is disposed beneath the aperture of the separation chamber. A gas permeable membrane extends across the channel such that a first portion of the membrane disposed at a top of the channel is located closer to the inlet than a second portion of the membrane disposed at a bottom of the channel.

In some embodiments, the gas permeable membrane further extends across the aperture such that the first portion of the membrane is located on a first side of the aperture closer to the inlet and the second portion of the membrane is located on a second side of the aperture opposite the first side and closer to the outlet In some embodiments, the gas permeable membrane comprises a hydrophobic material.

In one optional variation of these embodiments, the gas permeable membrane comprises a nonwoven spunbond olefin fiber material.

In one optional variation of these embodiments, the gas permeable membrane comprises at least one of polyvinylidene fluoride and polytetrafluoroethylene.

In some embodiments, a hydrophilic material fills the aperture in the separation chamber.

In some embodiments, a material fills the aperture, wherein the material comprises at least one of polyethersulfone, mixed cellulose ester, and cellulose acetate.

In some embodiments, the reservoir is attached by threads to the separation chamber.

In some embodiments, the apparatus further comprises a measurement device connected to the outlet of the separation chamber, the measurement device being configured to measure a property of the gas sample.

In one optional variation of these embodiments, the property of the gas sample is a carbon dioxide level in the gas sample.

In another aspect of the invention, an apparatus, comprises: a tube, having an inlet, an outlet, and an aperture disposed between the inlet and the outlet at a bottom of the tube, wherein the tube defines a channel extending in a first direction between the inlet and the outlet, the channel having a cross section perpendicular to the first direction; and a reservoir disposed beneath the aperture of the tube; and a gas permeable membrane extending across the channel at an angle greater than zero degrees with respect to the cross section of the channel.

In some embodiments, the angle is between 10 degrees and 80 degrees.

In some embodiments, the gas permeable membrane comprises a hydrophobic material.

In one optional variation of these embodiments, the gas permeable membrane comprises a nonwoven spunbond olefin fiber material.

In one optional variation of these embodiments, the gas permeable membrane comprises at least one of polyvinylidene fluoride and polytetrafluoroethylene.

In some embodiments, a hydrophilic material fills the aperture in the tube.

In some embodiments, a material fills the aperture, wherein the material comprises at least one of polyethersulfone, mixed cellulose ester, and cellulose acetate.

In some embodiments, the reservoir is attached by threads to the tube.

In some embodiments, a bag is disposed within the reservoir.

In some embodiments, the reservoir includes a transparent window by which a level of liquid contained within the reservoir may be viewed from outside the reservoir.

DETAILED DESCRIPTION

The present invention will now be described more fully hereinafter with reference to the accompanying drawings, in which preferred embodiments of the invention are shown. This invention may, however, be embodied in different forms and should not be construed as limited to the embodiments set forth herein. Rather, these embodiments are provided as teaching examples of the invention.

Figure 1:
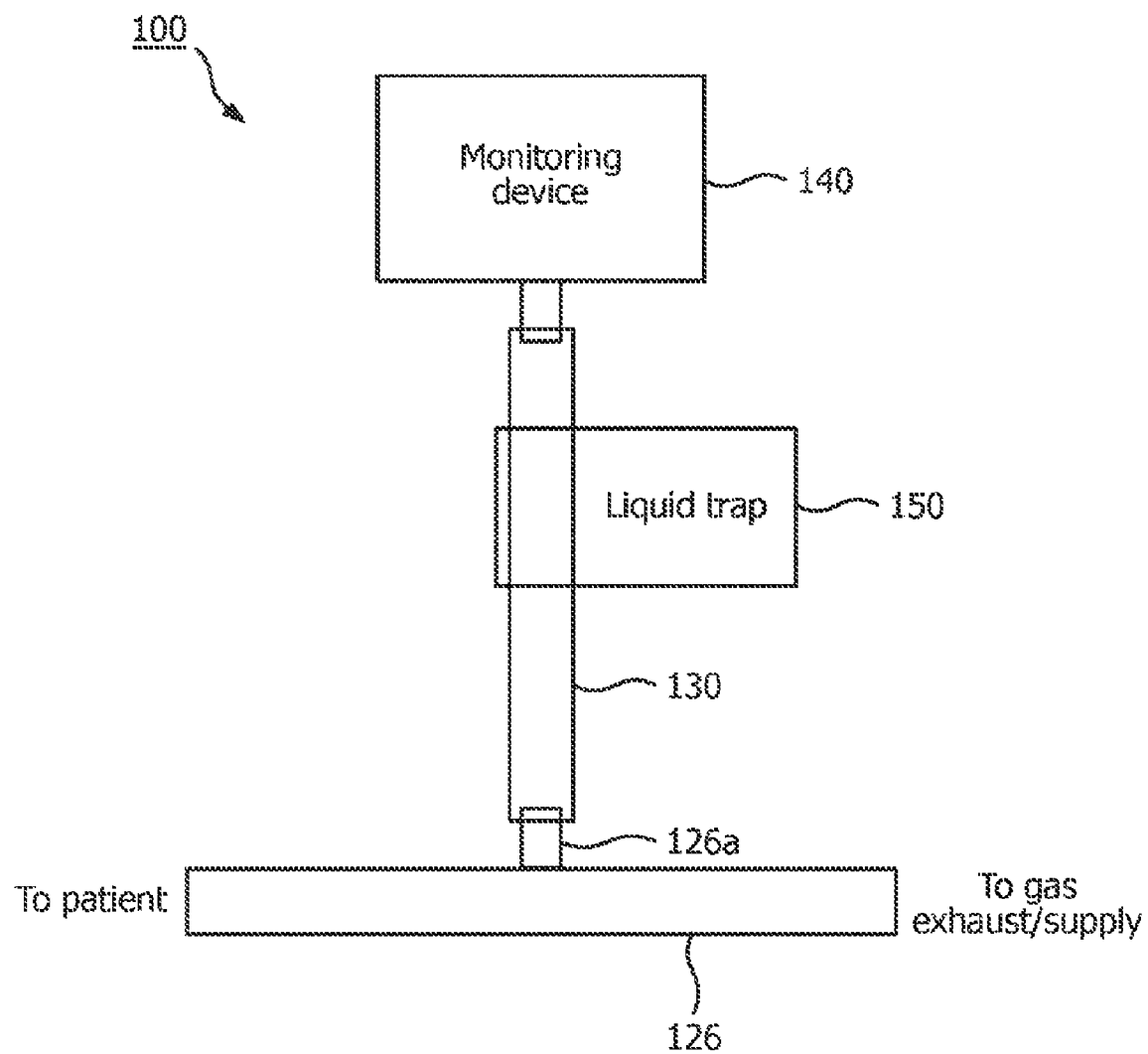
FIG. 1 illustrates one example embodiment of an arrangement which employs sidestream monitoring of a patient's respiratory gas.

FIG. 1 illustrates one example embodiment of an arrangement 100 which employs sidestream monitoring of a patient's respiratory gas. Arrangement 100 include a breathing tube 126 through which passes the respiratory gas of a patient. Tube 126 has a monitor port 126a which is connected via a tube 130 and a liquid trap 150 to a monitoring device 140.

In some embodiments, monitoring device 140 may comprise a capnography monitor. In particular, monitoring device 140 may include a sensor for measuring the $CO_2$ concentration in a gas sample, and a display for displaying the $CO_2$ concentration versus time or expired volume during the patient's respiratory cycle.

In operation, a sample of the respiratory gas from the patient is diverted via monitor port 126a to tube 130. Liquid may be mixed in with the gas sample, and water vapor in the gas sample may condense while passing through tube 130.

This liquid or water may negatively affect the sensor and/or other components of monitoring device 140.

Accordingly, liquid trap 150 captures liquid (e.g., water) mixed in the gas sample and prevents it from reaching monitoring device 140.

Figure 2A:
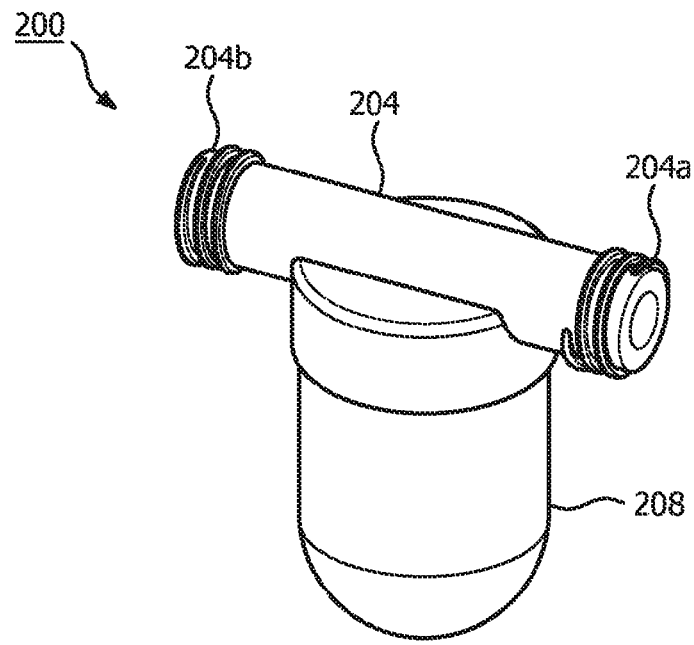
FIGS. 2A-B illustrate two views of one example embodiment of a liquid trap.
Figure 2B:
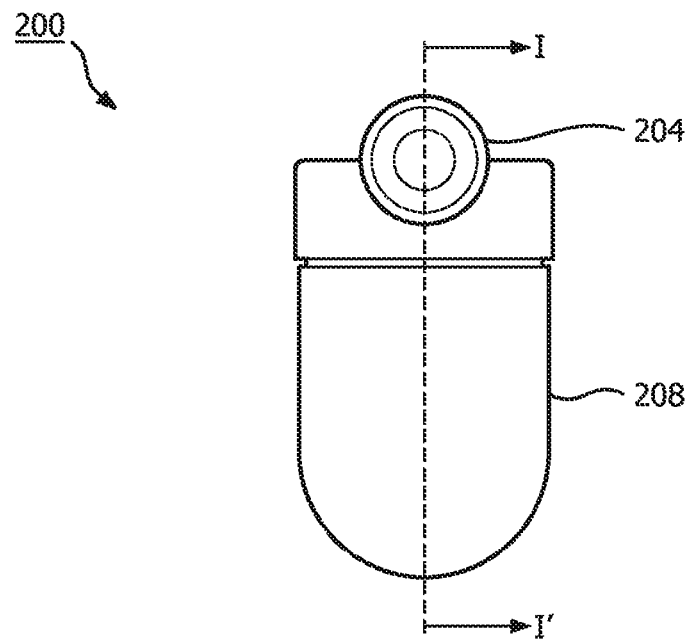

FIGS. 2A-B illustrate two views of one example embodiment of a liquid trap 200 which may be employed as the liquid trap 150 of arrangement 100. Liquid trap 200 includes a tube 204 and a reservoir 208. Tube 204 includes an inlet 204a configured to receive a gas sample from a patient; and an outlet 204b configured to output the gas sample, for example to a sensor, measurement instrument, or monitoring device such as a capnography monitor. Reservoir 208 captures and holds a liquid (e.g., condensed water) that is mixed with the gas sample which is received at inlet 204a so as to prevent it from passing to outlet 204b and thence, for example, to a sensor, measurement instrument, or monitoring device.

Figure 3:
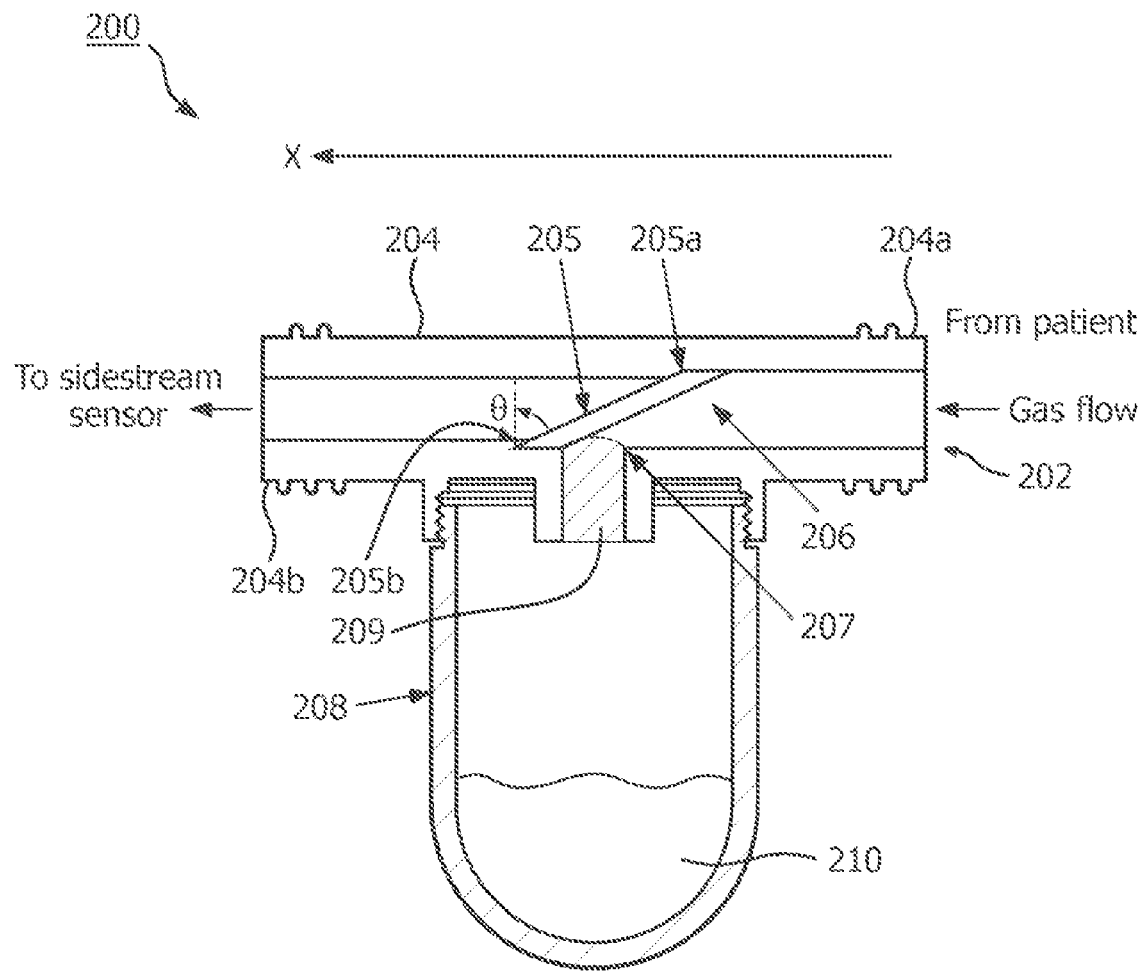
FIG. 3 illustrates a cutaway sectional view of the liquid trap of FIGS. 2A-B taken along line I-I' of FIG. 2B.

A better understanding of the configuration, construction, and operation liquid trap 200 can be had by reference to FIG. 3 which illustrates a cutaway sectional view of the liquid trap 200 taken along line I-I' of FIG. 2B. As shown in FIG. 3, tube 204 of liquid trap 200 defines a channel 206 extending in a first direction (labeled "X") between inlet 204a and outlet 204b. Channel 206 has a cross-section which extends perpendicular to the first direction. In the example embodiment liquid trap 200, the cross-section is circular, but in other embodiments of the liquid trap, the cross-section may have other shapes such as oblong, rectangular, or square. In some embodiments, the diameter of channel 206 may be about 0.100 inch.

Liquid trap 200 also includes a gas permeable membrane 205 extending across channel 206 such that a first portion 205a of membrane 205 which is disposed at a top of channel 206 is located closer to inlet 204a than a second portion 205b of membrane 205 which is disposed at a bottom of channel 206. In other words, membrane 205 is configured as a porous plug, or a ramp within channel 206 at an angle θ with respect to the cross-section of channel 206, where θ has some value other than zero degrees. In some embodiments, θ has a value between 10 and 80 degrees. In some embodiments, θ may be about 45 degrees. In some embodiments, the interior wall(s) of tube 204 which define channel 206 may include one or more notches or slots which are configured to hold gas permeable membrane 205 in position within channel 206.

Beneficially, gas permeable membrane 205 allows a gas sample to pass therethrough, preferably with minimal disruption, but inhibits or impedes the flow of liquid therethrough. In some embodiments, gas permeable membrane is porous with pore sizes ≥0.2 μm.

In some embodiments, gas permeable membrane 205 comprises a hydrophobic material. In some embodiments, gas permeable membrane 205 comprises a nonwoven spunbond olefin fiber material such as TYVEK®. In some embodiments, gas permeable membrane 205 comprises polyvinylidene fluoride (PVDF) and/or polytetrafluoroethylene (PTFE).

Tube 204 also has an aperture 207 disposed between inlet 204a and outlet 204b at a bottom of tube 204. Reservoir 208 is disposed beneath aperture 207. Beneficially aperture 207 has a sufficiently small size so as not to disturb the gas sample as it flows from inlet 204a to outlet 204b so as to allow accurate measurements of the gas at a sensor, measurement instrument, or monitoring device such as a capnography monitor. In some embodiments, aperture 207 has a diameter of about 0.06 inch or less.

In some embodiments, gas permeable membrane 205 extends across aperture 207 such that first portion 205a of membrane 205 is located on a first side of aperture 207 closer to inlet 204a and second portion 205b of membrane 205 is located on a second side of aperture 207 opposite the first side and closer to outlet 204b.

In some embodiments, liquid trap 200 includes a wick 209 filling aperture 207. An upper portion of wick 209 may contact the ramp formed by gas permeable membrane 205. Beneficially, wick 209 comprises a hydrophilic material. In some embodiments, the hydrophilic material comprises polyethersulfone, mixed cellulose ester, and/or cellulose acetate.

In other embodiments of liquid trap 200, wick 209 may be omitted, leaving aperture 207 open.

In operation, tube 204 operates as a separation chamber 202 for separating liquid (e.g., water) from the gas sample.

The gas sample flows through gas permeable membrane 205 and continues through separation chamber 202 to a sensor, measurement instrument, or monitoring device such as a capnography monitor.

However, as liquid (e.g., condensed water) flows through channel 206 it is impeded by gas permeable membrane 205. The ramp formed by gas permeable membrane 205, in conjunction with the flow rate and gravity forces the liquid down the ramp until it falls through aperture 207 disposed beneath the ramp formed by gas permeable membrane 205. When gas permeable membrane 205 comprises a hydrophobic material, this further impedes the flow of liquid through channel 206 of the separation chamber 202 to outlet 204b.

The liquid falls through the aperture 207 and collects in collection reservoir 208. When liquid trap 200 includes the hydrophilic wick 209, this aids in the removal of liquid from separation chamber 202 into reservoir 208. The collected liquid 210 accumulates in reservoir 208.

When the accumulated liquid 210 fills reservoir 208, then water trap 200 may be removed and disposed per an established protocol. In some embodiments, reservoir 208 is removably attached by threads to separation chamber 202. In that case, when accumulated liquid 210 fills reservoir 208, reservoir 208 may be detached from separation chamber 202 and either cleaned and replaced, or disposed of. In some embodiments, a bag may be disposed within reservoir 208 for collecting accumulated liquid 210. In that case, when accumulated liquid 210 fills reservoir 208, reservoir 208 may be detached from separation chamber 202, the bag may be disposed of, a new bag may be provided within reservoir 208, and then reservoir 208 may be reattached to separation chamber 202.

In some embodiments, reservoir 208 may be transparent, or may include a transparent window so that the level of accumulated liquid 210 contained within reservoir 208 may be viewed from outside reservoir 208, which may assist in determining when to remove and replace water trap 200, reservoir 208, or a bag disposed in reservoir 208, depending on a particular embodiment and established maintenance procedure.

Figure 4:
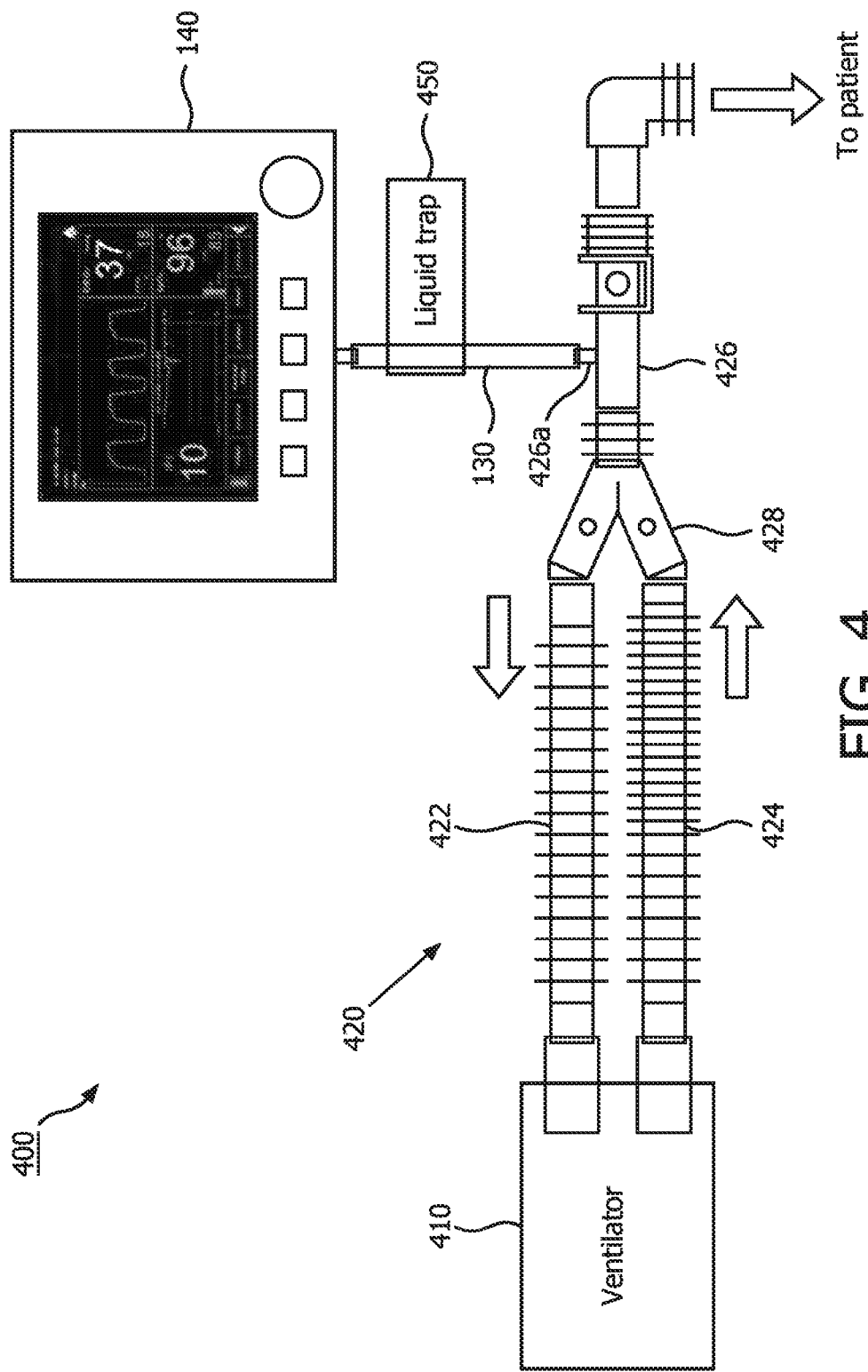
FIG. 4 illustrates one example embodiment of a ventilation arrangement which employs sidestream monitoring.

FIG. 4 illustrates one example embodiment of a ventilation arrangement 400 which employs sidestream monitoring. Ventilation arrangement 400 includes a ventilator 410, a dual limb patient circuit 420, a monitoring device 140, and a liquid trap 150. Dual-limb patient circuit 420 includes an inhalation patient circuit or inspiratory limb 422, and an exhalation patient circuit or expiratory limb 424, both of which are connected to a patient via a Y-connector 428 and a sidestream tap 426. Sidestream tap 426 has a monitor port 426a which is connected via tube 130 and liquid trap 450 to monitoring device 140. Liquid trap 200 described above may be employed as liquid trap 450 in arrangement 400. As noted above, in some embodiments, monitoring device 140 may comprise a capnography monitor. In particular, monitoring device 140 may include a sensor for measuring the $CO_2$ concentration in the gas sample, and a display for displaying the $CO_2$ concentration versus time or expired volume during the patient's respiratory cycle.

Figure 5:
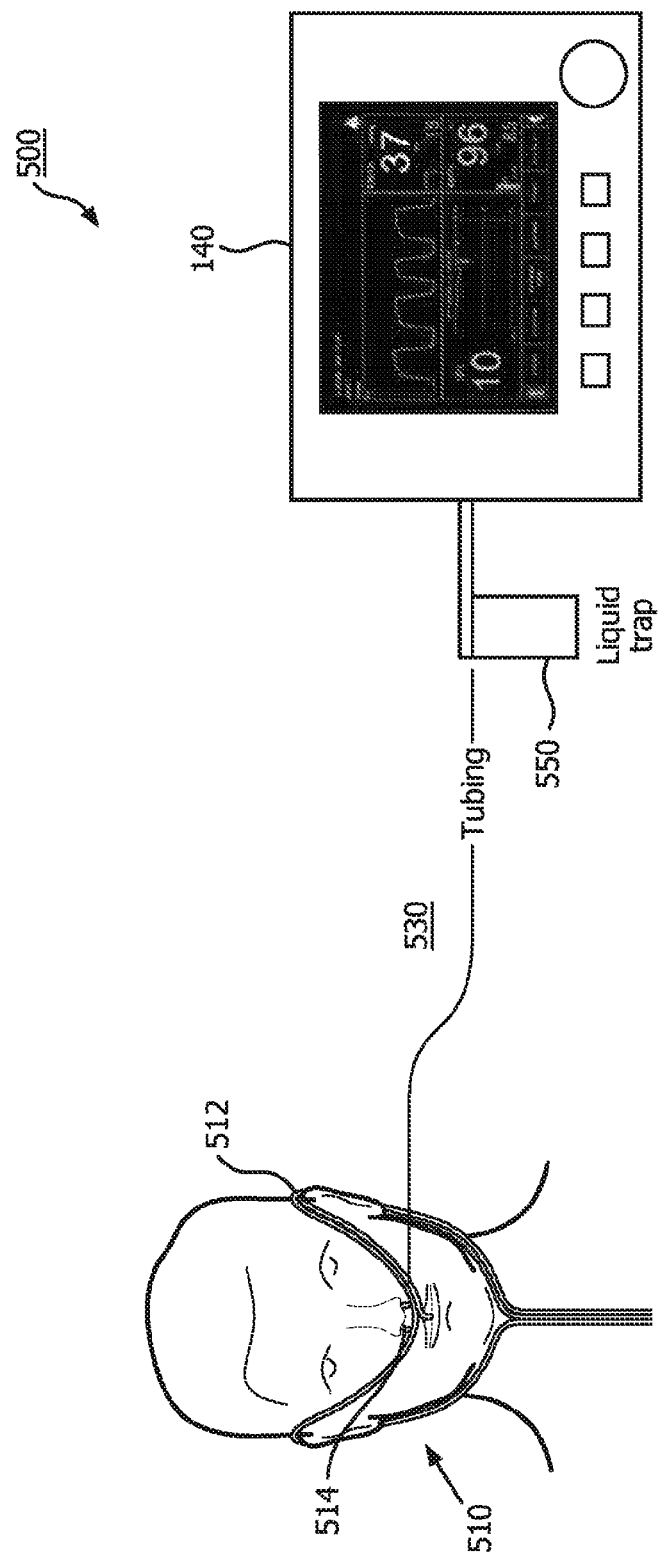
FIG. 5 illustrates a portion of one example embodiment of an arrangement which employs sidestream monitoring.

FIG. 5 illustrates a portion of one example embodiment of arrangement 500 which includes sidestream monitoring. In particular, in arrangement 500 one or more characteristics a gas sample from a non-intubated patient is measured via sidestream monitoring. Arrangement 500 includes a cannula assembly 510 which carries the respiratory gas of a patient. Cannula assembly 510 includes tubing assembly 512 and nasal prongs 514. Tubing 530 is connected to cannula assembly 510 and diverts a sample of the respiratory gas to monitoring device 140 via liquid trap. Liquid trap 200 described above may be employed as liquid trap 550 in arrangement 500. As noted above, in some embodiments, monitoring device 140 may comprise a capnography monitor. In particular, monitoring device 140 may include a sensor for measuring the $CO_2$ concentration in the gas sample, and a display for displaying the $CO_2$ concentration versus time or expired volume during the patient's respiratory cycle.

While preferred embodiments are disclosed herein, many variations are possible which remain within the concept and scope of the invention. Such variations would become clear to one of ordinary skill in the art after inspection of the specification, drawings and claims herein. The invention therefore is not to be restricted except within the scope of the appended claims.

What is claimed is:

1. An apparatus comprising:
a separation chamber defining a channel extending in a first direction between an inlet and an outlet and configured to pass a gas sample through the channel from the inlet to the outlet, the inlet being configured to receive the exhaled gas sample from a patient and the outlet configured to output the gas sample to a measurement device;
an aperture disposed at a bottom of the separation chamber between the inlet and the outlet;
a gas permeable membrane extending across the channel such that a first portion of the gas permeable membrane is disposed at a top of the channel and located closer to the inlet than a second portion of the membrane disposed at a bottom of the channel, the gas permeable membrane extending across the aperture such that the first portion of the gas permeable membrane is located on a first side of the aperture closer to the inlet and the second portion of the gas permeable membrane is located on a second side of the aperture opposite the first side and closer to the outlet; the gas permeable membrane being configured to separate liquid from the gas sample such that gas passes through the gas permeable membrane to the outlet and liquid is urged along the gas permeable membrane by gravity and the gas flowing through the gas permeable membrane to the aperture;
a reservoir disposed beneath the aperture and configured to accumulate the liquid separated from the gas sample by the gas permeable membrane; and
a hydrophilic material wick filling the aperture in the separation chamber in a bottom wall of the separation chamber and configured to move the liquid separated by the gas permeable membrane from the separation chamber to the reservoir.

2. The apparatus of claim 1, wherein the gas permeable membrane comprises a hydrophobic material.

3. The apparatus of claim 2, wherein the gas permeable membrane comprises a nonwoven spunbond olefin fiber material.

4. The apparatus of claim 2, wherein the gas permeable membrane comprises at least one of polyvinylidene fluoride and polytetrafluoroethylene.

5. The apparatus of claim 1, further comprising a material filling the aperture, wherein the material comprises at least one of polyethersulfone, mixed cellulose ester, and cellulose acetate.

6. The apparatus of claim 1, wherein the reservoir is attached by threads to the separation chamber.

7. The apparatus of claim 1, further comprising a measurement device connected to the outlet of the separation chamber, the measurement device being configured to measure a property of the gas sample.

8. The apparatus of claim 7, where the property of the gas sample is a carbon dioxide level in the gas sample.

9. The apparatus of claim 1, wherein the gas permeable membrane further extends across the aperture such that the first portion of the membrane is located on a first side of the aperture closer to the inlet and the second portion of the membrane is located on a second side of the aperture opposite the first side and closer to the outlet, wherein the membrane is along the gas permeable membrane is configured to separate liquid from the gas sample such that gas passes through the membrane to the outlet and liquid is forced along the gas permeable membrane by gravity and the gas flowing through the permeable membrane to the aperture.

10. The apparatus of claim 9, wherein a portion of the separation chamber between the gas permeable membrane and the outlet is aperture-free.

11. The apparatus according to claim 9, wherein the separation chamber is configured such that the gas sample does not exit the separation chamber and pass through the reservoir and re-enter the separation chamber.

12. The apparatus according to claim 9, wherein the separation chamber and reservoir are configured such that liquid accumulated in the reservoir is not re-entrained in the gas sample.

13. A liquid trap for capturing liquid in exhaled gas from a patient and blocking the liquid from reaching a downstream monitor for measuring a concentration of carbon dioxide (CO2) in the exhaled gas, the liquid trap comprising:
a tube defining a channel extending from an inlet end configured to receive the exhaled gas to an outlet and configured to be connected with the monitor;
a gas permeable membrane configured to pass a gas component of the exhaled gas and impede a flow of liquid therethrough mounted to the tube to divide the channel into an inlet portion and an outlet portion, a first portion of the gas permeable membrane being disposed at a top of the channel and a second portion disposed at a bottom of the channel, the first portion of the gas permeable membrane being closer to the inlet end than the second portion of the gas permeable membrane, the gas permeable membrane being configured to pass a gas component of the exhaled gas and impede a flow of liquid therethrough such that separated liquid flows down the gas permeable membrane due to gas flowing through the gas permeable membrane and gravitation forces;

a reservoir disposed beneath the tube and configured to accumulate the liquid;

an aperture defined in the tube only between the bottom side of the inlet portion of the channel and the reservoir such that the separated liquid that flows down the gas permeable membrane passes through the aperture and accumulates in the reservoir; and wherein the aperture is disposed beneath the gas permeable membrane and further including a hydrophilic wick disposed in the aperture to aid in removal of the separated liquid from the channel into the reservoir.

14. The liquid trap according to claim 13, wherein the outlet portion of the channel is free of apertures in communication with the reservoir.

15. The liquid trap according to claim 13, wherein the gas passes to the outlet from the inlet only via the gas permeable membrane and the channel.

16. The liquid trap according to claim 13, wherein the aperture is 0.06 inch or less in diameter so as not to disturb gas flow and further including:

a hydrophilic wick disposed in the aperture.

17. The liquid trap according to claim 1, wherein the channel is free of apertures in communication with the reservoir between the gas permeable membrane and the outlet.

* * * * *